(12) United States Patent
Hooven

(10) Patent No.: US 7,291,161 B2
(45) Date of Patent: Nov. 6, 2007

(54) ARTICULATED CLAMPING MEMBER

(75) Inventor: Michael D. Hooven, Cincinnati, OH (US)

(73) Assignee: AtriCure, Inc., West Chester, OH (US)

( * ) Notice: Subject to any disclaimer, the term of this patent is extended or adjusted under 35 U.S.C. 154(b) by 458 days.

(21) Appl. No.: 10/263,386

(22) Filed: Oct. 2, 2002

(65) Prior Publication Data

US 2004/0068274 A1    Apr. 8, 2004

(51) Int. Cl.
  A61B 17/00  (2006.01)
  A61B 17/08  (2006.01)
  A61B 18/18  (2006.01)

(52) U.S. Cl. .................. 606/205; 606/157; 606/52

(58) Field of Classification Search .................. 606/1, 606/157, 158, 142, 219
See application file for complete search history.

(56) References Cited

U.S. PATENT DOCUMENTS

| | | |
|---|---|---|
| 1,127,948 A | 2/1915 | Wappler |
| 2,004,559 A | 6/1935 | Wappler et al. |
| 3,470,875 A | 10/1969 | Johnson et al. |
| 3,630,207 A | 12/1971 | Kahn et al. .................. 128/350 |
| 3,862,630 A * | 1/1975 | Balamuth ........................ 606/1 |
| 3,868,957 A * | 3/1975 | Doddington ................ 606/158 |
| 3,901,242 A | 8/1975 | Storz ........................ 128/303 |
| 4,043,342 A | 8/1977 | Morrison, Jr. ............... 128/303 |
| 4,058,126 A * | 11/1977 | Leveen ........................ 606/158 |
| 4,106,508 A * | 8/1978 | Berlin ........................ 606/158 |
| 4,312,337 A | 1/1982 | Donohue |
| 4,353,371 A | 10/1982 | Cosman ...................... 128/303 |
| 4,492,231 A | 1/1985 | Auth ........................ 128/303 |
| 4,590,934 A | 5/1986 | Malis et al. ................. 128/303 |
| 4,706,667 A | 11/1987 | Roos .......................... 128/303 |
| 4,732,149 A | 3/1988 | Sutter ........................ 128/303 |
| 4,802,475 A | 2/1989 | Weshahy ...................... 128/303 |
| 4,848,338 A | 7/1989 | De Satnick et al. |
| 4,940,064 A | 7/1990 | Desai ......................... 128/784 |

(Continued)

FOREIGN PATENT DOCUMENTS

DE    43 13 903    9/1994

(Continued)

OTHER PUBLICATIONS

English abstract re Japanese Patent Application No. JP 1996000275351, published Apr. 28, 1997.

(Continued)

*Primary Examiner*—Julian W. Woo
(74) *Attorney, Agent, or Firm*—Cook, Alex, McFarron, Manzo, Cummings & Mehler, Ltd.

(57) ABSTRACT

A grasper is provided having a handle with an elongated shaft secured thereto. First and second jaw members with opposed clamping surfaces are secured to the shaft, with one jaw member being slidably secured with respect to the other jaw member. The jaw members are relatively movable by an actuator between an open position and a closed position. A resilient member is associated with at least one of the first or second jaw members or the actuator limits the force exerted on tissue held between the clamping surfaces of the jaws when the jaws are in the closed position. The jaws are preferably, but not necessarily, pivotal relative to the elongated shaft by remote actuation.

29 Claims, 5 Drawing Sheets

U.S. PATENT DOCUMENTS

| | | | |
|---|---|---|---|
| 4,976,721 A | 12/1990 | Blasnik et al. | |
| 5,009,661 A | 4/1991 | Michelson | |
| 5,013,312 A | 5/1991 | Parins et al. | 606/37 |
| 5,033,477 A | 7/1991 | Chin et al. | |
| 5,044,947 A | 9/1991 | Sachdeva et al. | |
| 5,071,428 A | 12/1991 | Chin et al. | |
| 5,083,565 A | 1/1992 | Parins | 128/642 |
| 5,085,657 A | 2/1992 | Ben-Simhon | 606/42 |
| 5,087,243 A | 2/1992 | Avitall | 604/20 |
| 5,116,332 A | 5/1992 | Lottick | 606/42 |
| 5,125,928 A | 6/1992 | Parins et al. | |
| 5,147,355 A | 9/1992 | Friedman | 606/23 |
| 5,190,541 A * | 3/1993 | Abele et al. | 606/50 |
| 5,207,691 A | 5/1993 | Nardella | 606/142 |
| 5,217,460 A | 6/1993 | Knopfler | 606/52 |
| 5,231,995 A | 8/1993 | Desai | 128/784 |
| 5,242,441 A | 9/1993 | Avitall | 606/41 |
| 5,242,458 A | 9/1993 | Bendel et al. | |
| 5,250,047 A | 10/1993 | Rydell | 606/48 |
| 5,250,075 A | 10/1993 | Badie | 606/207 |
| 5,254,130 A | 10/1993 | Poncet et al. | |
| 5,263,493 A | 11/1993 | Avitall | 607/122 |
| 5,269,326 A | 12/1993 | Verrier | 128/642 |
| 5,269,780 A | 12/1993 | Roos | 606/42 |
| 5,281,215 A | 1/1994 | Milder | 606/20 |
| 5,281,216 A | 1/1994 | Klicek | 606/42 |
| 5,293,869 A | 3/1994 | Edwards et al. | 128/642 |
| 5,306,234 A | 4/1994 | Johnson | |
| 5,318,589 A | 6/1994 | Lichtman | 606/205 |
| 5,323,781 A | 6/1994 | Ideker et al. | |
| 5,327,905 A | 7/1994 | Avitall | 128/772 |
| 5,354,297 A | 10/1994 | Avitall | 606/45 |
| 5,357,956 A | 10/1994 | Nardella | 128/642 |
| 5,397,339 A | 3/1995 | Desai | 607/116 |
| 5,403,312 A | 4/1995 | Yates et al. | 606/50 |
| 5,423,807 A | 6/1995 | Milder | 606/20 |
| 5,429,131 A | 7/1995 | Scheinman et al. | 128/642 |
| 5,429,636 A | 7/1995 | Shikhman et al. | 606/41 |
| 5,438,302 A | 8/1995 | Goble | 331/167 |
| 5,441,483 A | 8/1995 | Avitall | 604/95 |
| 5,443,463 A | 8/1995 | Stern et al. | 606/51 |
| 5,445,638 A | 8/1995 | Rydell et al. | 606/51 |
| 5,449,355 A | 9/1995 | Rhum et al. | |
| 5,449,365 A | 9/1995 | Green et al. | |
| 5,451,223 A | 9/1995 | Ben-Simhon | 606/42 |
| 5,451,227 A | 9/1995 | Michaelson | |
| 5,452,733 A | 9/1995 | Sterman et al. | |
| 5,454,370 A | 10/1995 | Avitall | 128/642 |
| 5,465,716 A | 11/1995 | Avitall | 128/642 |
| 5,472,441 A | 12/1995 | Edwards et al. | 606/41 |
| 5,478,309 A | 12/1995 | Sweezer et al. | 604/4 |
| 5,480,409 A | 1/1996 | Riza | 606/205 |
| 5,487,385 A | 1/1996 | Avitall | 128/642 |
| 5,496,312 A | 3/1996 | Klicek | 606/34 |
| 5,500,011 A | 3/1996 | Desai | 607/116 |
| 5,500,012 A | 3/1996 | Brucker et al. | |
| 5,507,773 A | 4/1996 | Huitema et al. | |
| 5,531,744 A | 7/1996 | Nardella et al. | 606/48 |
| 5,536,267 A | 7/1996 | Edwards et al. | 606/41 |
| 5,549,636 A | 8/1996 | Li | |
| 5,555,883 A | 9/1996 | Avitall | 128/642 |
| 5,562,699 A | 10/1996 | Heimberger et al. | |
| 5,562,700 A | 10/1996 | Huitema et al. | |
| 5,562,721 A | 10/1996 | Marchlinski et al. | 607/99 |
| 5,564,440 A | 10/1996 | Swartz et al. | 128/898 |
| 5,571,215 A | 11/1996 | Sterman et al. | |
| 5,575,766 A | 11/1996 | Swartz et al. | |
| 5,575,805 A | 11/1996 | Li | |
| 5,582,609 A | 12/1996 | Swanson et al. | 606/39 |
| 5,587,723 A | 12/1996 | Otake et al. | 345/118 |
| 5,595,183 A | 1/1997 | Swanson et al. | 128/697 |
| 5,599,350 A | 2/1997 | Schulze et al. | 606/51 |
| 5,611,813 A | 3/1997 | Lichtman | 606/205 |
| 5,620,459 A | 4/1997 | Lichtman | 606/205 |
| 5,642,736 A | 7/1997 | Avitall | 128/772 |
| 5,655,219 A | 8/1997 | Jusa et al. | 370/338 |
| 5,672,174 A | 9/1997 | Gough et al. | 606/41 |
| 5,674,220 A | 10/1997 | Fox et al. | 606/51 |
| 5,680,860 A | 10/1997 | Imran | |
| 5,683,384 A | 11/1997 | Gough et al. | 606/41 |
| 5,687,737 A | 11/1997 | Branham et al. | 128/710 |
| 5,688,270 A | 11/1997 | Yates et al. | 606/51 |
| 5,690,611 A | 11/1997 | Swartz et al. | 604/53 |
| 5,693,051 A | 12/1997 | Schulze et al. | 606/51 |
| 5,697,925 A | 12/1997 | Taylor | 606/34 |
| 5,697,928 A | 12/1997 | Walcott et al. | 606/41 |
| 5,702,359 A | 12/1997 | Hofmann et al. | 604/20 |
| 5,702,390 A | 12/1997 | Austin et al. | 606/48 |
| 5,702,438 A | 12/1997 | Avitall | 607/122 |
| 5,709,680 A | 1/1998 | Yates et al. | 606/50 |
| 5,718,703 A | 2/1998 | Chin | 606/49 |
| 5,722,403 A | 3/1998 | McGee et al. | 128/642 |
| 5,725,512 A | 3/1998 | Swartz et al. | 604/280 |
| 5,728,143 A | 3/1998 | Gough et al. | 607/101 |
| 5,730,127 A | 3/1998 | Avitall | 128/642 |
| 5,730,704 A | 3/1998 | Avitall | 600/374 |
| 5,733,280 A | 3/1998 | Avitall | |
| 5,735,847 A | 4/1998 | Gough et al. | 606/45 |
| 5,735,849 A | 4/1998 | Baden et al. | 606/51 |
| 5,740,808 A | 4/1998 | Panescu et al. | 128/662 |
| 5,755,664 A | 5/1998 | Rubenstein | 600/377 |
| 5,755,717 A | 5/1998 | Yates et al. | 606/51 |
| 5,759,158 A | 6/1998 | Swanson | 600/508 |
| 5,766,177 A | 6/1998 | Lucas-Dean et al. | |
| 5,776,130 A | 7/1998 | Buysse et al. | |
| 5,779,727 A * | 7/1998 | Orejola | 606/174 |
| 5,782,397 A | 7/1998 | Koukline | |
| 5,782,827 A | 7/1998 | Gough et al. | 606/41 |
| 5,782,828 A | 7/1998 | Chen et al. | 606/42 |
| 5,785,706 A | 7/1998 | Bednarek | 606/41 |
| 5,797,906 A | 8/1998 | Rhum et al. | 606/48 |
| 5,797,960 A | 8/1998 | Stevens et al. | 606/213 |
| 5,800,484 A | 9/1998 | Gough et al. | 607/104 |
| 5,807,393 A | 9/1998 | Williamson, IV et al. | 606/32 |
| 5,807,395 A | 9/1998 | Mulier et al. | 606/41 |
| 5,810,804 A | 9/1998 | Gough et al. | 606/41 |
| 5,810,805 A | 9/1998 | Sutcu et al. | 606/45 |
| 5,810,811 A | 9/1998 | Yates et al. | 606/50 |
| 5,814,028 A | 9/1998 | Swartz et al. | |
| 5,817,091 A | 10/1998 | Nardella et al. | 606/38 |
| 5,823,955 A | 10/1998 | Kuck et al. | 600/374 |
| 5,823,956 A | 10/1998 | Roth et al. | 600/374 |
| 5,829,447 A | 11/1998 | Stevens et al. | 128/898 |
| 5,833,690 A | 11/1998 | Yates et al. | 606/52 |
| 5,833,703 A | 11/1998 | Manushakian | 606/174 |
| 5,842,984 A | 12/1998 | Avitall | 600/374 |
| 5,843,075 A | 12/1998 | Taylor | 606/34 |
| 5,843,122 A | 12/1998 | Riza | 606/207 |
| 5,846,238 A | 12/1998 | Jackson et al. | 606/41 |
| 5,849,011 A | 12/1998 | Jones et al. | |
| 5,849,020 A | 12/1998 | Long et al. | 606/167 |
| 5,853,411 A | 12/1998 | Whayne et al. | 606/41 |
| 5,855,590 A | 1/1999 | Malecki et al. | |
| 5,855,614 A | 1/1999 | Stevens et al. | 623/11 |
| 5,860,975 A | 1/1999 | Goble et al. | 606/45 |
| 5,863,290 A | 1/1999 | Gough et al. | 606/41 |
| 5,863,291 A | 1/1999 | Schaer | 606/41 |
| 5,868,737 A | 2/1999 | Taylor et al. | 606/34 |
| 5,871,483 A | 2/1999 | Jackson et al. | 606/41 |
| 5,873,896 A | 2/1999 | Ideker | 607/14 |
| 5,876,398 A | 3/1999 | Mulier et al. | |
| 5,876,400 A | 3/1999 | Songer | 606/45 |
| 5,876,401 A | 3/1999 | Schulze et al. | 606/51 |
| 5,891,135 A | 4/1999 | Jackson et al. | 606/41 |

| | | | | | | |
|---|---|---|---|---|---|---|
| 5,891,136 A | 4/1999 | McGee et al. ............... 606/41 | | 6,264,087 B1 | 7/2001 | Whitman |
| 5,891,138 A | 4/1999 | Tu et al. | | 6,267,761 B1 | 7/2001 | Ryan |
| 5,893,863 A | 4/1999 | Yoon ............... 606/170 | | 6,273,887 B1 | 8/2001 | Yamauchi et al. |
| 5,897,554 A | 4/1999 | Chia et al. | | 6,277,117 B1 | 8/2001 | Tetzlaff et al. |
| 5,899,898 A | 5/1999 | Arless et al. ............... 606/22 | | 6,292,678 B1 | 9/2001 | Hall et al. |
| 5,899,899 A | 5/1999 | Arless et al. ............... 606/22 | | 6,296,640 B1 | 10/2001 | Wampler et al. |
| 5,902,289 A | 5/1999 | Swartz et al. ............... 604/281 | | 6,311,692 B1 | 11/2001 | Vaska et al. |
| 5,910,129 A | 6/1999 | Koblish et al. ............... 604/95 | | 6,314,962 B1 | 11/2001 | Vaska et al. |
| 5,913,855 A | 6/1999 | Gough et al. ............... 606/41 | | 6,314,963 B1 | 11/2001 | Vaska et al. |
| 5,921,924 A | 7/1999 | Avitall ............... 600/374 | | 6,332,089 B1 | 12/2001 | Acker et al. |
| 5,921,983 A * | 7/1999 | Shannon, Jr. ............... 606/50 | | 6,334,860 B1 | 1/2002 | Dorn |
| 5,924,424 A | 7/1999 | Stevens et al. ............... 128/898 | | 6,334,861 B1 | 1/2002 | Chandler et al. |
| 5,925,038 A | 7/1999 | Panescu et al. ............... 606/41 | | 6,356,790 B1 | 3/2002 | Maguire et al. |
| 5,925,042 A | 7/1999 | Gough et al. ............... 606/41 | | 6,358,249 B1 | 3/2002 | Chen et al. |
| 5,925,050 A | 7/1999 | Howard, III | | 6,391,024 B1 | 5/2002 | Sun et al. |
| 5,928,229 A | 7/1999 | Gough et al. ............... 606/41 | | 6,443,970 B1 | 9/2002 | Schulze et al. |
| 5,931,836 A | 8/1999 | Hatta et al. ............... 606/38 | | 6,447,507 B1 | 9/2002 | Bednarek et al. |
| 5,935,126 A | 8/1999 | Riza ............... 606/51 | | 6,464,700 B1 | 10/2002 | Koblish et al. |
| 5,938,660 A | 8/1999 | Swartz et al. ............... 606/45 | | 6,474,340 B1 | 11/2002 | Vaska et al. |
| 5,941,251 A | 8/1999 | Panescu et al. ............... 128/899 | | 6,488,678 B2 | 12/2002 | Sherman |
| 5,941,845 A | 8/1999 | Tu et al. ............... 604/53 | | 6,488,680 B1 | 12/2002 | Francischelli et al. |
| 5,944,718 A | 8/1999 | Austin et al. ............... 606/48 | | 6,506,189 B1 | 1/2003 | Rittman, III et al. |
| 5,947,938 A | 9/1999 | Swartz et al. ............... 604/280 | | 6,517,536 B2 | 2/2003 | Hooven |
| 5,951,547 A | 9/1999 | Gough et al. ............... 606/41 | | 6,540,740 B2 | 4/2003 | Lehmann et al. |
| 5,951,552 A | 9/1999 | Long et al. ............... 606/46 | | 6,546,935 B2 | 4/2003 | Hooven |
| 5,954,665 A | 9/1999 | Ben-Haim ............... 600/515 | | 6,558,385 B1 * | 5/2003 | McClurken et al. ............ 606/50 |
| 5,961,514 A | 10/1999 | Long et al. ............... 606/41 | | 6,575,969 B1 | 6/2003 | Rittman, III et al. |
| 5,967,976 A | 10/1999 | Larsen ............... 600/374 | | 6,610,055 B1 | 8/2003 | Swanson et al. |
| 5,971,983 A | 10/1999 | Lesh ............... 606/41 | | 6,632,222 B1 | 10/2003 | Edwards et al. |
| 5,972,026 A | 10/1999 | Laufer et al. ............... 607/96 | | 6,679,882 B1 | 1/2004 | Kornerup |
| 5,980,516 A | 11/1999 | Mulier et al. ............... 606/41 | | 6,692,491 B1 | 2/2004 | Phan |
| 5,980,517 A | 11/1999 | Gough ............... 606/41 | | 2001/0031961 A1 | 10/2001 | Hooven |
| 5,984,281 A | 11/1999 | Hacker et al. ............... 261/71 | | 2001/0039419 A1 | 11/2001 | Francischelli et al. |
| 5,997,533 A | 12/1999 | Kuhns ............... 606/41 | | 2002/0002329 A1 | 1/2002 | Avitall |
| 6,001,096 A * | 12/1999 | Bissinger et al. ............... 606/50 | | 2002/0019629 A1 | 2/2002 | Dietz et al. |
| 6,010,516 A | 1/2000 | Hulka ............... 606/148 | | 2002/0032440 A1 | 3/2002 | Hooven |
| 6,010,531 A | 1/2000 | Donlon et al. ............... 623/2 | | 2002/0052602 A1 | 5/2002 | Wang et al. |
| 6,012,457 A | 1/2000 | Lesh ............... 128/898 | | 2002/0082595 A1 | 6/2002 | Langberg et al. |
| 6,013,074 A | 1/2000 | Taylor ............... 606/34 | | 2002/0091382 A1 | 7/2002 | Hooven |
| 6,016,809 A | 1/2000 | Mulier et al. ............... 128/898 | | 2002/0091383 A1 | 7/2002 | Hooven |
| 6,017,358 A | 1/2000 | Yoon et al. ............... 606/205 | | 2002/0091384 A1 | 7/2002 | Hooven |
| 6,023,638 A | 2/2000 | Swanson ............... 600/510 | | 2002/0099364 A1 | 7/2002 | Lalonde |
| 6,024,740 A | 2/2000 | Lesh et al. ............... 606/34 | | 2002/0103484 A1 | 8/2002 | Hooven |
| 6,024,741 A | 2/2000 | Williamson, IV et al. ... 606/40 | | 2002/0107513 A1 | 8/2002 | Hooven |
| 6,030,403 A | 2/2000 | Long et al. ............... 606/185 | | 2002/0107514 A1 | 8/2002 | Hooven |
| 6,033,402 A | 3/2000 | Tu et al. | | 2002/0115990 A1 | 8/2002 | Acker |
| 6,036,670 A | 3/2000 | Wijeratne et al. ............... 604/96 | | 2002/0115993 A1 | 8/2002 | Hooven |
| 6,039,731 A | 3/2000 | Taylor et al. ............... 606/34 | | 2002/0120263 A1 | 8/2002 | Brown et al. |
| 6,039,733 A | 3/2000 | Buysse et al. | | 2002/0120316 A1 | 8/2002 | Hooven |
| 6,039,748 A | 3/2000 | Savage et al. ............... 606/180 | | 2002/0128643 A1 | 9/2002 | Simpson et al. |
| 6,047,218 A | 4/2000 | Whayne et al. ............... 607/122 | | 2003/0004507 A1 | 1/2003 | Francischelli et al. |
| 6,048,329 A | 4/2000 | Thompson et al. ............ 604/95 | | 2003/0009094 A1 | 1/2003 | Segner et al. |
| 6,050,996 A | 4/2000 | Schmaltz et al. | | 2003/0018329 A1 | 1/2003 | Hooven |
| 6,064,902 A | 5/2000 | Haissaguerre et al. | | 2003/0028187 A1 | 2/2003 | Vaska et al. |
| 6,068,653 A | 5/2000 | LaFontaine | | 2003/0032952 A1 | 2/2003 | Hooven |
| 6,071,281 A | 6/2000 | Burnside et al. | | 2003/0045871 A1 | 3/2003 | Jain et al. |
| 6,083,150 A | 7/2000 | Aznoian et al. | | 2003/0050557 A1 | 3/2003 | Susil et al. |
| 6,083,222 A | 7/2000 | Klein et al. | | 2003/0060822 A1 | 3/2003 | Schaer et al. |
| 6,096,037 A | 8/2000 | Mulier et al. | | 2003/0069572 A1 | 4/2003 | Wellman et al. |
| 6,110,098 A | 8/2000 | Renirie et al. ............... 600/16 | | 2003/0069577 A1 | 4/2003 | Vaska et al. |
| 6,113,595 A | 9/2000 | Muntermann | | 2003/0073991 A1 | 4/2003 | Francischelli |
| 6,113,598 A | 9/2000 | Baker | | 2003/0078570 A1 | 4/2003 | Heiner et al. |
| 6,117,101 A | 9/2000 | Diederich et al. | | 2003/0078574 A1 | 4/2003 | Hall et al. |
| 6,123,703 A | 9/2000 | Tu et al. | | 2003/0093068 A1 | 5/2003 | Hooven |
| 6,126,658 A | 10/2000 | Baker | | 2003/0093104 A1 | 5/2003 | Bonner et al. |
| 6,142,994 A | 11/2000 | Swanson et al. | | 2003/0097124 A1 | 5/2003 | Lehmann et al. |
| 6,156,033 A | 12/2000 | Tu et al. | | 2003/0100895 A1 | 5/2003 | Simpson et al. |
| 6,161,543 A | 12/2000 | Cox et al. | | 2003/0114844 A1 | 6/2003 | Ormsby et al. |
| 6,162,220 A | 12/2000 | Nezhat | | 2003/0120268 A1 | 6/2003 | Bertolero et al. |
| 6,187,003 B1 | 2/2001 | Buysse et al. | | 2003/0125726 A1 | 7/2003 | Maguire et al. |
| 6,193,713 B1 | 2/2001 | Geistert et al. | | 2003/0125729 A1 | 7/2003 | Hooven |
| 6,193,716 B1 | 2/2001 | Shannon, Jr. | | 2003/0125730 A1 | 7/2003 | Berube et al. |
| 6,237,605 B1 | 5/2001 | Vaska et al. | | 2003/0130598 A1 | 7/2003 | Manning et al. |

| | | |
|---|---|---|
| 2003/0135207 A1 | 7/2003 | Langberg et al. |
| 2003/0144657 A1 | 7/2003 | Bowe et al. |
| 2003/0158548 A1 | 8/2003 | Phan et al. |
| 2003/0171745 A1 | 9/2003 | Francischelli et al. |
| 2003/0178032 A1 | 9/2003 | Ingle et al. |

FOREIGN PATENT DOCUMENTS

| | | |
|---|---|---|
| EP | 0 450 608 | 10/1991 |
| EP | 0 765 639 | 4/1997 |
| WO | WO 92/05828 | 4/1992 |
| WO | WO 93/25267 A1 | 12/1993 |
| WO | WO 97/10764 | 3/1997 |
| WO | WO 97/32525 | 9/1997 |
| WO | WO 98/17187 | 4/1998 |
| WO | WO 98/53750 | 12/1998 |
| WO | WO 99/02096 | 1/1999 |
| WO | WO 99/04696 | 2/1999 |
| WO | WO 99/12487 | 3/1999 |
| WO | WO 99/44519 | 9/1999 |
| WO | WO 99/56644 | 11/1999 |
| WO | WO 99/56648 | 11/1999 |
| WO | WO 99/59486 | 11/1999 |
| WO | WO 00/21449 | 4/2000 |
| WO | WO 00/27310 A2 | 5/2000 |
| WO | WO 00/27310 A3 | 5/2000 |
| WO | WO 00/27311 | 5/2000 |
| WO | WO 00/27312 | 5/2000 |
| WO | WO 00/27313 | 5/2000 |
| WO | WO 00/42931 | 7/2000 |
| WO | WO 00/42932 | 7/2000 |
| WO | WO 00/42933 | 7/2000 |
| WO | WO 00/42934 | 7/2000 |
| WO | WO 01/82812 A1 | 11/2001 |
| WO | WO 01/82813 A2 | 11/2001 |
| WO | WO 01/82813 A3 | 11/2001 |
| WO | WO 02/087454 A1 | 11/2002 |

OTHER PUBLICATIONS

Yoshio Kosakai, M.D. et al., "Cox Maze Procedure for Chronic Atrial Fibrillation Associated with Mitral Valve Disease," The Journal of Thoracic and Cardiovascular Surgery, 1994; vol. 108, No. 6, pp. 1049-1055.
Ki-Bong Kim, M.D. et al., Abstract "The Cox-Maze III Procedure for Atrial Fibrillation Associated with Rheumatic Mitral Valve Disease," The Annals Of Thoracic Surgery, 2000; pp. 1-5.
Hiroshi Nakagawa, et al., Abstract, "Creation of Long Linear Transmural Radiofrequency Lesions in Atrium Using a Novel Spiral Ribbon—Saline Irrigated Electrode Catheter," Journal of American College of Cardiology, Feb. 1996.
Taijiro Sueda, et al., "Efficacy of a Simple Left Atrial Procudure for Chronic Atrial Procedure for Chronic Atrial Procedure for Chronic Atrial Fibrillation in Mitral Valve Operations," The Annals of Thoracic Surgery, 1997, vol. 63, pp. 1070-1073.
Re: Dr. Adam E. Saltman, New Program in Surgical Electrophysiology Established, Interet Website of Departmental News, Dept. of Surgery, University Hospital & Medical Center, Stony Brook State University of New York (www.informatics.synysb.edu/surgery/electro-news.html); 2000, pp. 1-2.
Mien-Cheng Chen, M.D., et al., "Radiofrequency and Cryoablation of Atrial Fibrillation in Patients Undergoing Valvular Operations," Anals of Thoracic Surgery, 1998:65:1666-1672.
Arif Elvan, M.D., et al., Abstract, "Radiofrequency Catheter Ablation of the Atria Reduces Inducibility and Duration of Atrial Fibrillation in Dogs," CIRCULATION, 1995:91:2235-2244.
Warren M. Jackman, M.D., et al., "Radiofrequency Current Directed Across the Mitral Anulus With a Bipolar Epicardial-Endocardial Catheter Electrode Configuration in Dogs," CIRCULATION, 1988; vol. 78, No. 5, pp. 1288-1297.
Lauren Neegaard, "Slicing a Heart to Make It Beat," Article from The Associated Press, Mar. 26, 1998 Website (www.nando.com/newsroom/ntn/health/032698/health24_22737_body.html).
Yoshito Inoue, et al., "Video Assisted Thoracoscopic and Cardioscopic Radiofrequency Maze Ablation," ASAIO Journal, 1997, pp. 334-337.
Yoshito Inoue, et al., Abstract, "Video Assisted Thoracoscopic and Cardioscopic Radiofrequency Maze Ablation," ASAIO Journal, 1997.
Mary O. Palazzo, RN, MS, CCRN, "What You Need To Know—a-fib 101," from the Atrial Fibrillation Page Website (www.members.aol.com/mazern/afib101.htm) Jun. 5, 2000.
Mary O. Palazzo, RN, MS, CCRN, "What You Need To Know—maze FAQ," from the Atrial Fibrillation Page Website (www.members.aol.com/mazern/mazefaq.htm) Nov. 25, 1999.
Mary O. Palazzo, RN, MS, CCRN, "What You Need To Know—maze FAQ," from the Atrial Fibrillation Page Website (www.members.aol.com/mazern/mazefaq.htm) Jun. 21, 2000.
Stuart P. Thomas, et al., "Mechanism, Localization and Cure of Atrial Arrhythmias Occuring After a New Intraoperative Endocardial Radiofrequency Ablation Procedure for Atrial Fibrillation," Journal of the American College of Cardiology, 2000, vol. 35, No. 2, pp. 442-450.
Akira T. Kawaguchi et al., "Factors Affecting Rhythm After the Maze Procedure for Atrial Fibrillation," CIRCULATION, 1998. vol. 78, No. 5, pp. 1288-1296.
Ivan M. Robbins, M.D., et al., "Pulmonary Vein Stenosis After Catheter Ablation of Atrial Fibrillation," CIRCULATION, 1998; 98:1769-1775.
Enrique, J. Berjano, et al., "Bipolar Electrosurgery With Long Electrodes for RF Coagulation of Atrial Tissue," Proceedings 19th International Conference—IEEE/EMBS Oct. 30-Nov. 2, 1997 Chicago, Ill. USA, pp. 2528-2530.
Taijiro Sueda et al., "Simple Left Atrial Procedure for Chronic Atrial Fibrillation Associated with Mitral Valve Disease," The Annals of Thoracic Surgery, 1996;62:1796-1800.
Cox, James L., M.D., Ed., "Seminars in Thoracic and Cardiovascular Surgery: The Maze Procedure for Atrial Fibrillation," Official Publication of the American Association for Thoracic Surgery, vol. 12, No. 1, 2000.
European Patent Office Supplemental European Search Report dated Feb. 7, 2006 (3 pages).

* cited by examiner

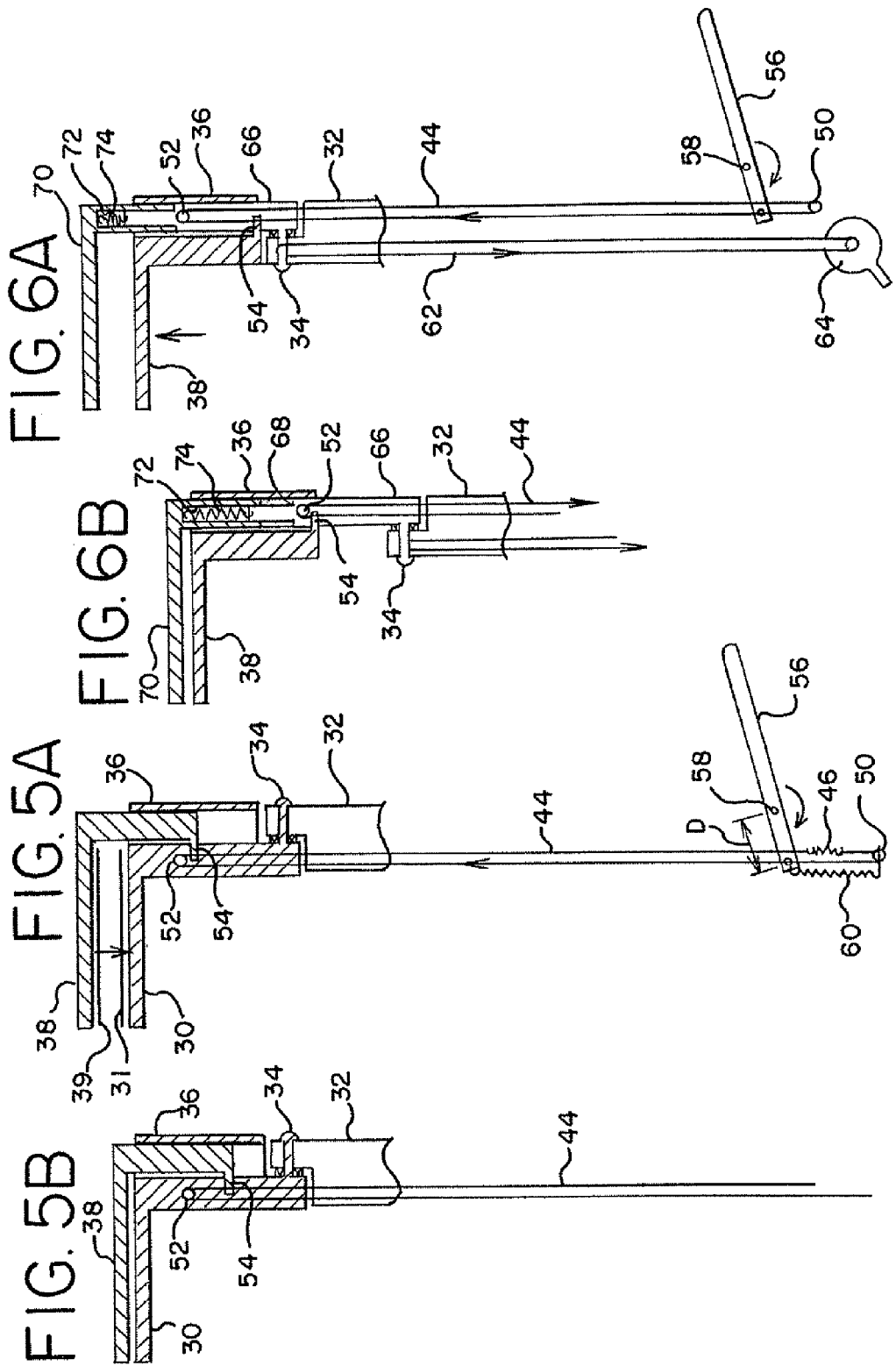

ARTICULATED CLAMPING MEMBER

BACKGROUND OF THE INVENTION

Devices for grasping and/or clamping tissue between a pair of opposed jaw members are widely used in a variety of surgical procedures. Depending upon the procedure to be performed, it may be difficult to both gain access to and properly clamp the desired tissue due to the angle of the jaws with respect to the shaft to which they are attached. Consequently, surgical graspers have been developed in which the jaws are pivotally secured to the shaft so that the jaw assembly may be articulated with regard to the shaft. See, for example, U.S. Pat. No. 5,507,773.

One complication in providing for articulating jaws on a grasper is providing an actuation mechanism to move the jaws between the open and closed positions. Such an actuation mechanism must function reliably without undue interference with the articulation joint, and it is preferred that the actuation mechanism not require enlargement of the cross-sectional area of the grasper shaft.

It is also desirable in various procedures for the jaws to provide a constant, predetermined clamping pressure that is not dependent upon the force the surgeon applies to the grasper handle. This is of particular significance where the jaws of the grasper include RF energy electrodes for ablating or cauterizing tissue. In such devices a uniform, consistent clamping pressure results in a more predictable and even application of electrosurgical current to the clamped tissue.

Accordingly, it is one object of the present invention to provide a tissue graspers or clamping device whose jaws are pivotable with respect to their supporting shaft so that the surgeon may more easily grasp the desired tissue.

It is also an object of another aspect of the present invention to provide a tissue grasper or clamping device with articulatable jaws that allows control of the maximum pressure that is applied to the tissue held between the jaws.

It is a further object to provide a tissue grasper with articulatable jaws wherein the actuation mechanism for the jaws is sufficiently small that the grasper shaft can accommodate electrical conductors, sensors, and the like in addition to the actuation mechanism without necessitating undue enlargement of the cross-section of the grasper shaft.

These objects are by way of example and not limitation of the invention claimed. As claimed, the invention may address one or more of the above objects or may address other concerns or achieve other benefits not set forth above.

SUMMARY OF THE INVENTION

The present invention is generally embodied in a clamp or grasper having a handle with an elongated shaft secured thereto. First and second jaw members with opposed clamping surfaces are secured to the shaft, with one of the jaw members being movable with respect to the other jaw member. The jaw members are movable between an open position, in which the clamping surfaces are spaced apart, and a closed position, in which the clamping surfaces are spaced apart an amount less than that in the open position.

The jaws may be activated by an actuating member(s), such as a rod or cable, that extends from the handle, through the elongated shaft and operable directly or indirectly on at least one of the jaw members for moving the jaw members between the open and closed positions. An actuator, such as a knob, lever, trigger, or other device may be secured to the handle and connected directly or indirectly to the actuating member for actuating the member. A resilient or biasing means or element, such as an elastic segment or a spring, may be associated with at least one of the first or second jaw members or the activating member to regulate or control the force exerted on tissue held between the clamping surfaces of the jaws when the jaws are in the closed position. The jaws are preferably, but not necessarily, pivotably mounted to the elongated shaft for articulation, and are pivotable with respect thereto by remote actuation.

In one embodiment, a fixed jaw is mounted and pivotal with respect to an elongated shaft and has a sleeve member associated therewith. A movable jaw is slidably secured by the sleeve. An actuating member, which optionally may be in the form of a cable, extends from the handle through the elongated shaft and is secured to the movable jaw, with an acutator trigger pivotably secured to the handle and also connected to the cable. A resilient or biasing member, such as a spring or elastic member, is interposed between the cable and the movable jaw so that manipulation of the trigger actuates the cable to move the movable jaw between an open and closed position with respect to the fixed jaw, the spring regulating the amount of force exerted on tissue held between the jaws when the movable jaw is in the closed position. Further, an additional spring or similar resilient mean may be disposed between the jaws. The springs may have different spring constraints so that, for example, when the jaws are closing, the spring located between the jaws compresses or expands before the other spring compresses or expands.

In a further embodiment, the movable jaw is slidably carried by the fixed jaw, and an actuating member in the form of cable extends in a loop between the handle and the fixed jaw, around a first pulley associated with the handle and a second pulley associated with the fixed jaw. The cable is secured to both an actuator, such as a trigger, and the movable jaw so that pivoting the trigger or otherwise moving the actuator moves the cable and, therefore, the movable jaw between open and closed positions with respect to the fixed jaw. A spring may be interposed along the loop of cable in order to regulate the amount of force exerted on tissue held between the jaws when the movable jaw is in the closed position.

In a still further embodiment, a jaw mount is carried by the elongated shaft. Both first and second jaws are movably situated on the mount. An actuator, such as a trigger, is carried by the handle and an actuating member controls jaw movement. The member may comprise a cable forming a loop that extends between handle and the mount, and that is trained about a first pulley associated with the handle and a second pulley associated with the mount. The cable is secured to both the actuator and the second jaw so that movement of the actuator, e.g., pivoting the trigger, moves the second jaw between an open and closed position with respect to the first jaw. A spring or other resilient member may be interposed between the first jaw and the mount to regulate the amount force exerted on tissue held between the jaws when the second jaw is moved to the closed position.

In another embodiment, a jaw mount is carried by the shaft with both first and second jaw members slidably carried by the mount. An actuator, e.g., a trigger is movably mounted to the handle and an actuating member, such as a cable, connects the actuator to the second jaw for moving the second jaw from an open to a closed position with respect to the first jaw. A first spring is interposed between the second jaw and the mount, which biases the second jaw toward the open position. A second spring is interposed between the first jaw and the mount for biasing the first jaw toward the second jaw and for regulating the amount of force exerted on tissue held between the jaws when the second jaw is moved to the closed position.

In another embodiment, the fixed jaw is pivotally secured to the shaft, with a sleeve slidably secured to the fixed jaw. A movable jaw is slidably received in the sleeve and an actuating member, preferably in the form of a length of cable, forms a loop that extends between the handle and the fixed jaw. The cable is trained about a first pulley associated with the handle and a second pulley associated with the fixed jaw. The cable is secured to both an actuator, e.g., a trigger, and the sleeve so that moving the actuator (pivoting the trigger) moves the sleeve and the movable jaw carried thereby, between open and closed positions respect to the fixed jaw. A biasing member such as a spring is interposed between the sleeve and the movable jaw for biasing the movable jaw toward the fixed jaw and for regulating the amount of force exerted on tissue held between the jaws when the movable jaw is moved to the closed position.

In a further embodiment, the fixed jaw has a sleeve slidably associated therewith and is pivotally secured to the elongated shaft. The movable jaw is carried by the sleeve, and a cable or other actuating member connects an actuator to the movable jaw for moving the movable jaw between a closed position and an open position. A spring or other biasing member is interposed between the fixed jaw and the movable jaw to bias the movable jaw toward the closed position and to regulate the amount of force exerted on tissue held between the jaws when the second jaw is in the closed position.

In another embodiment, the grasper includes a fixed jaw with a sleeve slidably associated therewith secured to the shaft. A movable jaw is slidably received by the sleeve, and a length of cable is secured to a trigger and forms a loop extending between the handle and the fixed jaw. The cable is trained about a first pulley associated with the handle and a second pulley associated with the fixed jaw. An actuator associated with the fixed jaw and secured to the cable is movable between first and second positions with respect to the fixed jaw by pivoting the trigger member. A spring is interposed between the actuator and the movable jaw so that the actuator is moved between the first and second positions, with the movable jaw being moved between open and closed positions. The spring regulates the force exerted on tissue held between the jaws when the jaw is moved to the closed position.

The above summaries are for introductory purposes only and are not intended to be exhaustive or exclusive of all embodiments of the present invention, or to identify any required features or aspects of the present invention.

BRIEF DESCRIPTION OF THE DRAWINGS

FIGS. 5A and 5B are fragmentary, cross-sectional views of a fourth embodiment of an actuation mechanism according to the present invention showing the jaws in the open and closed positions, respectively.

FIGS. 6A and 6B are fragmentary, cross-sectional views of a fifth embodiment of an actuation mechanism according to the present invention showing the jaws in the open and closed positions, respectively.

DETAILED DESCRIPTION

The present invention has particular but not exclusive utility in connection with grasping or clamping devices for use in open or minimally invasive surgical procedures. The present invention has added benefits in grasping or clamping devices that include bipolar RF energy electrodes on the opposed jaw clamping surfaces, such as shown and described in U.S. patent application Ser. No. 10/032,378, filed Oct. 26, 2001, which is incorporated herein by reference.

The device disclosed in the referenced application is intended for use as a grasper which can create transmural ablation lesions in cardiac tissue for treatment, for example, of atrial fibrillation. In such treatment, ablation lesion lines may be formed in a pre-arranged pattern in the tissue of the heart to block aberrant electrical signals. The creation of this particular pattern is generally referred to as the Maze procedure. Among other things, the Maze procedure requires a series of transmural ablations or lesions to be formed on the atrium in the vicinity of the pulmonary veins.

Figure 1:
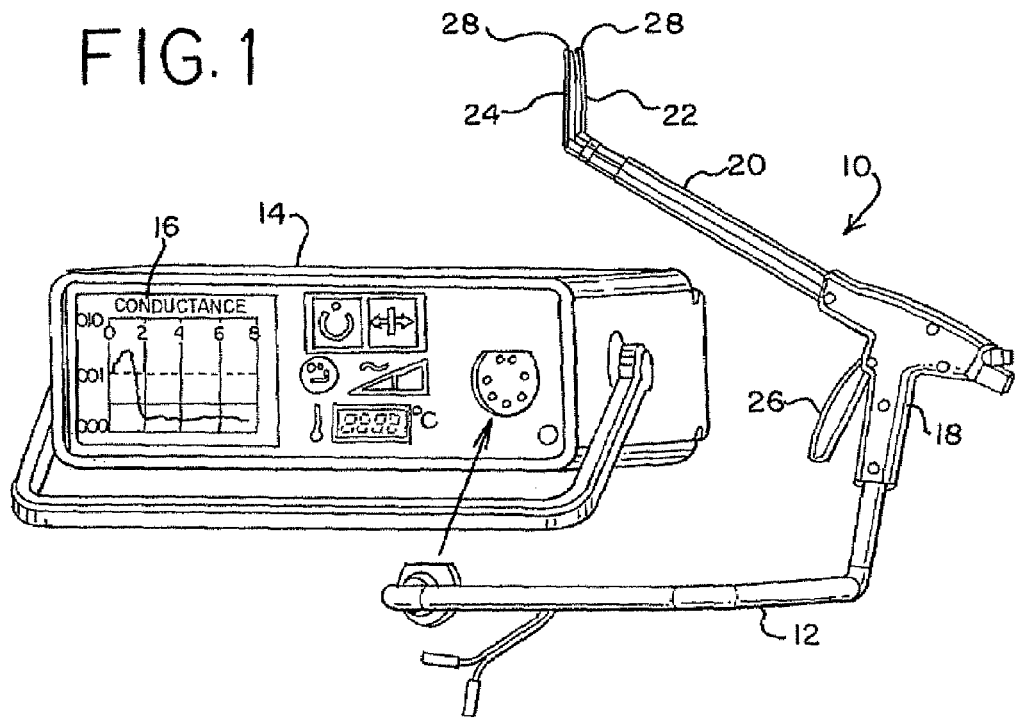
FIG. 1 is a perspective view of a tissue grasper with articulatable jaw members of the type that may incorporate the present invention.

The present invention is generally embodied in a grasping or clamping device 10 (FIG. 1) that is particularly useful for creating the various transmural lesions in cardiac tissue required by the Maze and other procedures, whether a minimally invasive or open chest procedure is used for the treatment of atrial fibrillation. The clamping or grasping device will be referred to as a "grasper" for convenience only, and that term is intended to include devices for clamping, pinching, grasping tissue. The grasper 10 includes a cord 12 for housing conductors (not shown) and for plugging into an electrosurgical RF generator 14 to provide current to the grasper 10. The generator 14 typically includes a display 16 to provide a visual indication of the degree of conductance of the tissue being ablated.

The grasper 10 includes a handle 18 that has an elongated shaft 20 attached thereto. The shaft 20 is preferably malleable so that it can be bent by the surgeon into a configuration that more easily permits grasping of the desired tissue, although a rigid shaft may be more preferred for other procedures. Opposed parallel jaws or jaw assemblies 22 and 24 may be pivotably secured, directly or indirectly, to the distal end of the shaft 20. The jaws 22 and 24 are relatively movable between a spaced-apart open position and a closed position, where they are closer, preferably although not necessarily contacting each other. The jaws may be moved between open and closed positions by means of an actuator and/or actuator member such as a lever or trigger 26 pivotably mounted to the handle 18 and operatively connected to at least one of the jaws. The spacing between the jaws 22 and 24 is preferably substantially uniform or constant, and the facing jaw surfaces parallel, particularly when in the closed position.

Each jaw assembly 22 and 24 has a facing surface to clamp or compress tissue between the jaws, and an elongated electrode 28 located along the facing surface to contact the clamped tissue and provide an electrical pathway contacting the tissue to be ablated. In other words, the electrode is located on the "inside" of its jaw assembly (the "inside" being defined as the side that contacts the tissue to be ablated).

Each of the electrodes 28 is attached to an electrically conductive means, such as a wire that runs the length of the shaft 20 and through the conductor cord 12 or coupling to the RF generator 14.

In order to ablate a narrow, long region of biological tissue with the instrument 10, the tissue is placed between the open instrument jaws 22 and 24. The user then moves the actuator, e.g. actuation trigger or lever 26, to close the jaws on the tissue. The operator then activates the RF generator 14 and RF energy passes through the tissue grasped between the electrodes 28, ablating the tissue between the electrodes and forming an elongated transmural lesion in the tissue. After the completion of ablation, the operator releases the actuator, allowing the jaws to part and releasing the clamping of the tissue. The jaw members 22 and 24 return to their open position, as does the actuator or actuation lever.

Figure 2B:
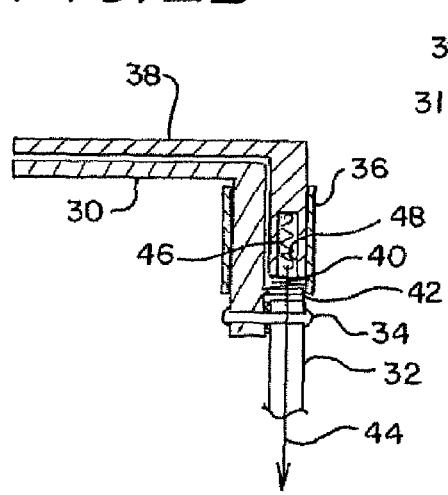
FIGS. 2A and 2B are fragmentary, cross-sectional views of a first embodiment of an actuation mechanism according to the present invention showing the jaws in the open and closed positions, respectively.
Figure 2A:
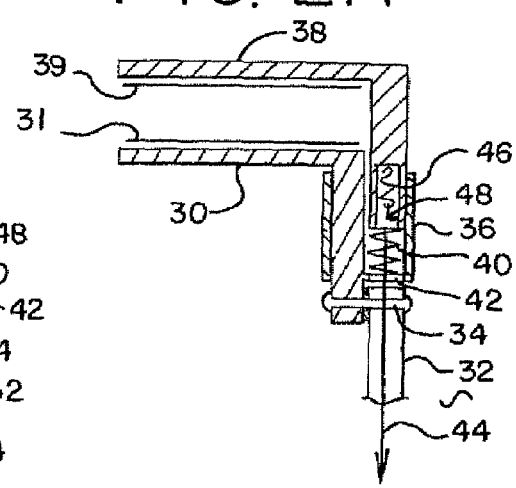

In accordance with one aspect of the present invention, the jaws are articulated relative to the shaft 20. In accordance with another aspect of the invention, the device includes means for limiting or controlling the clamping pressure exerted by the jaws. These aspects of the present invention may be used together or separately. With reference to FIGS. 2A and 2B, there is seen a first embodiment of the articulated grasper jaws in accordance with one or more aspects of the present invention. As illustrated, an inner, fixed jaw member 30 is pivotally secured to the grasper shaft 32 by a pin or rivet 34, although other means for pivotal mounting may be used without departing from the present invention. If articulation is not needed, the jaw member 30 can be fixed to the grasper shaft.

A separate tubular sleeve member 36 is secured to the fixed jaw 30. The sleeve member 36 has an interior region that slidably receives the outer, movable jaw member 38. The fixed and movable jaw members 30 and 38 have facing surfaces each of which carries a continuous elongated bipolar electrodes 31 and 39, respectively, as described above and which, for clarity, are shown in diagrammatic form. A compression spring 40 is captured within the sleeve 36 between an extending arm 42 on the fixed jaw 30 and the movable jaw member 38. The spring 40 biases the movable jaw member 38 away from the fixed jaw member 30 to the open position shown in FIG. 2A.

A mechanism is preferably provided for remotely moving the movable jaw member 38 to the closed position shown in FIG. 2B. To this end, an actuating member, which may be in the form of a length of cable 44, extends from the handle through the shaft 32. The cable 44 can be of any flexible material, metal or plastic, single or multiple strand, and preferably has a low coefficient of friction. The cable 44 is attached on one end to the actuator, illustrated as actuating lever 26, and on the other end to the movable jaw member 38.

In order to control the force exerted on tissue captured between the closed jaws 30 and 38, a resilient member, such as a tension spring 46, is interposed between the cable 44 and the movable jaw 38. It may also be located at other positions along the length of the cable, as described later.

Tension spring 46 is such that it limits the pulling force that can be exerted by the actuating lever on the movable jaw to between about 2 lbs. and 20 lbs., and preferably to about a force of 7 lbs. This translates to pressure against the cardiac tissue held between the jaws of about 7 psi to 70 psi and preferably about 25 psi. As illustrated, the tension spring 46 is received in a recess 48 in the movable jaw member 38. Thus, as tension is applied to the cable 44 by actuation of the lever, the movable jaw member 38 is pulled toward the fixed jaw member 30 against the force of the compression spring 40 and to the position shown in FIG. 2B. The tension spring 46 is simultaneously stretched, thus regulating the amount of force exerted on tissue captured between the jaw members 30 and 38, and also allowing various amounts of jaw closure, depending on the thickness of the tissue being clamped. For example, with thicker tissue the tension spring allows the jaws to be spaced farther apart than when clamping thinner tissue. Once tension on the cable 44 is released, the compression spring 40 returns the movable jaw member 38 to the open position shown in FIG. 2A.

For a tension spring 46 with a spring constant of $K_t$, the pulling force applied by the cable to the movable jaw is the product of the spring constant and the distance $D_t$, that the spring is stretched. It should be noted that pulling force exerted by the cable on the lower jaw is opposed by the force exerted by the compression spring 40, which is the product of the spring constant for the compression spring $K_c$ and the distance it is compressed $D_c$. Thus, the net force exerted on the heart tissue by the movable jaw is the difference between these forces or the quantity $(K_t D_t - K_c D_c)$. By selecting the spring constants and the amount of stretch or compression permitted, the force exerted on the cardiac tissue may be controlled or limited as desired. In this embodiment, the spring constant $K_c$ of the compression spring is preferably lower than the spring constant $K_t$ of the tension spring.

Figure 3A:
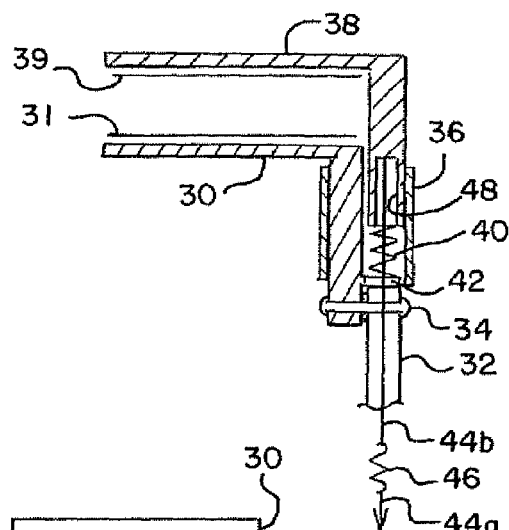
FIGS. 3A and 3B are fragmentary, cross-sectional views of a second embodiment of actuation mechanism according to the present invention showing the jaws in the open and closed positions, respectively.
Figure 3B:
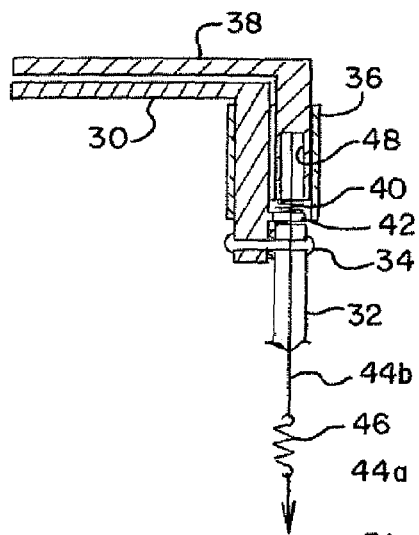

A second embodiment of the actuation mechanism for a grasper in accordance with one or more aspects of the present invention is shown in FIGS. 3A and 3B. The embodiment of FIGS. 3A and 3B is similar in certain respects to structure and operation to that of FIGS. 2A and 2B, and the same reference numerals are used with respect to both embodiments. In FIGS. 3A and 3B, the tension spring 46 is not received in the recess 48 in the movable jaw member 38. Instead, the tension spring 46 is located along the cable 44, and may be located within the shaft 32, with a first length of cable 44a connecting the tension spring 46 to the actuator lever, and a second length of cable 44b connecting the tension spring 46 to the movable jaw member 38.

Figure 4A:
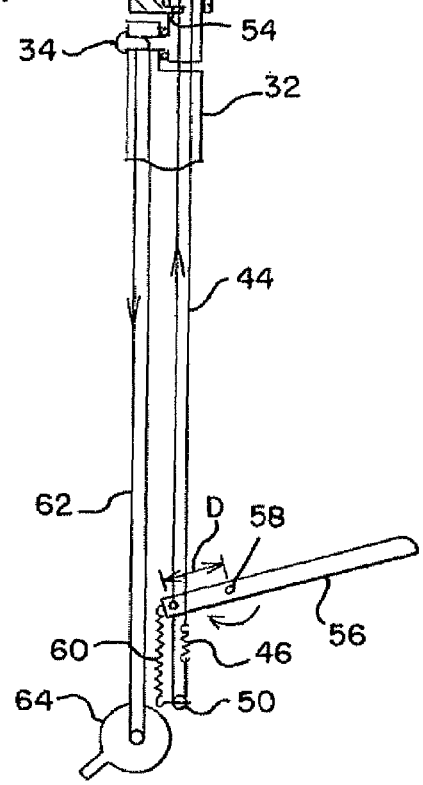
FIGS. 4A and 4B are fragmentary, cross-sectional views of a third embodiment of an actuation mechanism according to the present invention showing the jaws in the open and closed positions, respectively.
Figure 4B:
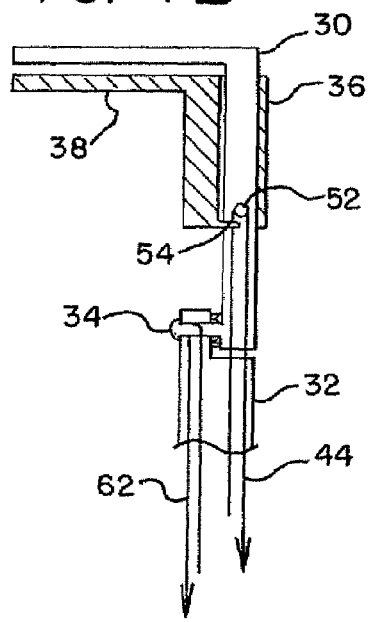

A third embodiment of an actuation mechanism for a grasper embodying one or more aspects of the present invention is seen in FIGS. 4A and 4B, and identical reference numerals to those used in connection with FIGS. 2-3 are used to designate corresponding elements. As in the above embodiments, the jaws may be generally L-shaped with a tissue clamping portion (which mounts electrodes 31 and 39) and a right angle portion that serves to mount the jaws in their proper relationship to the shaft and/or the other jaw.

A fixed jaw member 30 is pivotally secured to the grasper shaft 32 by a pin or rivet 34 or similar device preferably formed integrally with the fixed jaw 30. A movable jaw member 38 is slidably secured to the fixed jaw member 30 by means of a sleeve member 36 formed integrally with the movable jaw.

To effect movement of the movable jaw member 38 between the open and closed positions, a length of cable 44 in the form an endless loop extends between the handle, where it is trained or looped about a first pulley, pin or the like 50, and the fixed jaw member 30, where it is trained or looped about a second pulley or pin 52 fixed to the jaw 30. The cable 44 is secured to an arm 54 on the movable jaw and to the actuator lever or trigger 56 at a distance D displaced from the pivot 58 for the trigger 56. Accordingly, as the trigger 56 rotates about the pivot 58, it pulls the cable 44 so that it moves about the pulleys 50 and 52 to move the movable jaw to the fixed jaw.

In keeping with another aspect of the invention, a tension spring 46 is interposed in the endless loop of cable 44. With a fixed maximum movement of the trigger, the tension spring serves to regulate or limit the maximum force that can exerted on tissue held between the closed jaws. As illustrated, the tension spring 46 is located within the handle. However, it could be located anywhere along the portion of the cable 44 that acts to close the jaw members. A further spring 60 is interposed between the lever 56 and the handle to bias the lever in a direction so that tension is placed on the cable 44 to return the movable jaw member 38 and lever to the open position shown in FIG. 4A.

For remotely pivoting the jaw members 30 and 38 with respect to the grasper shaft 32, the grasper in FIGS. 4A and 4B includes a pivoting assembly. To this end, a second loop of cable 62 is secured on one end to the pivot pin 34 that secures the fixed jaw to the grasper shaft 32 and on its other end to a second actuator device such as trigger 64 pivotally mounted to the handle. Pivoting of the second trigger 64 with respect to the handle rotates the cable 62, and thus the pivot pin 34, to remotely change the angle of the grasper jaws 30 and 38 with respect to the shaft 32. The cable 62 may engage the pin by friction, by meshing gears between the cable and pin, by direct attachment or other mechanical designs so that movement of the cable causes pivoting of the pin and attached jaws. While this mechanism for remotely pivoting the jaw members of the grasper is shown in connection with only selected embodiments of the invention, it is equally adaptable for use with all disclosed articulated embodiments.

A fourth embodiment of an actuation mechanism for a grasper according the present invention is shown in FIGS. 5A and 5B. The embodiment of FIGS. 5A and 5B is similar to that of FIGS. 4A and 4B, and similar reference numerals are used for designating corresponding elements. The device of FIGS. 5A and 5B differs from that of FIGS. 4A and 4B in that the inner jaw member comprises the fixed jaw member 30 that is pivotally secured to the grasper shaft 32, while the outer jaw member comprises the movable jaw member 38 slidably mounted to the fixed jaw member 30. Additionally, the embodiment of FIGS. 5A and 5B does not include the mechanism for remotely pivoting the jaw members 30 and 38 with respect to the grasper shaft 32. Otherwise, the structure, function and operation of the device of FIGS. 5A and 5B is substantially identical to that of FIGS. 4A and 4B.

Turning to FIGS. 6A and 6B, there seen a fifth embodiment of graspers embodying one or more aspects of the present invention. This embodiment is similar in many respects to that shown in FIGS. 4A and 4B, and like reference numerals are used to designate corresponding structure. A mounting structure, preferably but not necessarily in the form of an elongated post or rod 66, is pivotally secured to the grasper shaft 32 by a pin 34 formed integrally with the post 66. The post 66 has a smaller diameter or relieved terminal portion defining a shoulder 68. The "fixed" jaw member 70 has a recessed area or bore 72 in the jaw member for slidably receiving the distal portion of the post. A movable jaw member 38 is slidably secured to the post 66 by means of a sleeve member 36 preferably formed integrally with the movable jaw.

To effect movement of the movable jaw member 38 between the open and closed positions, a length of cable 44 in the form of an endless loop extends between pulley 50 in the handle and pulley 52 fixed to the post 66. The cable 44 is secured to an arm 54 on the movable jaw 38 and to a trigger or lever 56 secured by pivot 58 to the handle. Accordingly, as the trigger 56 is pivoted to move the cable about the pulleys 50 and 52, and the arm 54, and consequently the movable jaw 38, are moved therewith.

In order to regulate or limit the maximum force that can be exerted on tissue held between the closed jaws, a tension spring 74 is interposed between the distal end of post 66 and the fixed jaw member 70. As illustrated, the tension spring 74 resides in the hollow recess or bore 72 formed in the fixed jaw member 70. As the movable jaw member 38 is moved from the open position shown in FIG. 6A and tissue is grasped between the jaws 38 and 70, the fixed jaw 70 is allowed to slide along the distal end of post 66 against the force of spring 74. When the jaws 38 and 70 are opened, the spring 74 returns the fixed jaw 70 to its original position shown in FIG. 6A, with the fixed jaw 70 seated on the shoulder 68 on the relieved area of the post 66. Thus, although referred to as the fixed jaw, jaw 70 is movable to the extent permitted by biasing spring 74 which serves to limit the compressive force on the tissue. As used herein and in the claims, "fixed jaw" is not intended to preclude any movement and is intended to include possible movement such as may occur in the embodiment of FIGS. 6A and 6B. As can be seen in FIGS. 6A and 6B, the main movable jaw 38 is the jaw directly moved by the operator via trigger 56 and cable 44. The fixed jaw 70 moves as a result of force exerted on the tissue by movable jaw 38 and as permitted by spring 74.

The embodiment of FIGS. 6A and 6B also includes an actuation mechanism for pivoting the jaw members 38 and 70 with respect to the shaft 32. This mechanism is identical to that shown in FIGS. 4A and 4B, and, consequently, is not discussed in detail.

Figure 7A:
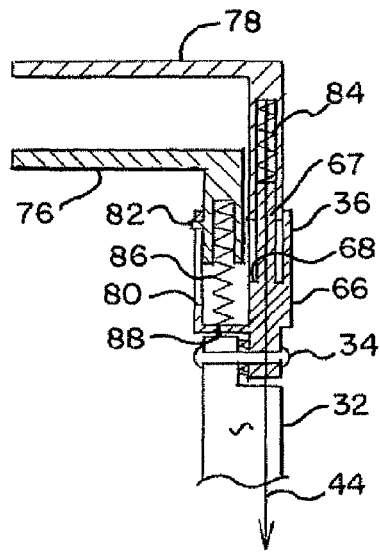
FIGS. 7A and 7B are fragmentary, cross-sectional views of a sixth embodiment of an actuation mechanism according to the present invention showing the jaws in the open and closed positions, respectively.
Figure 7B:
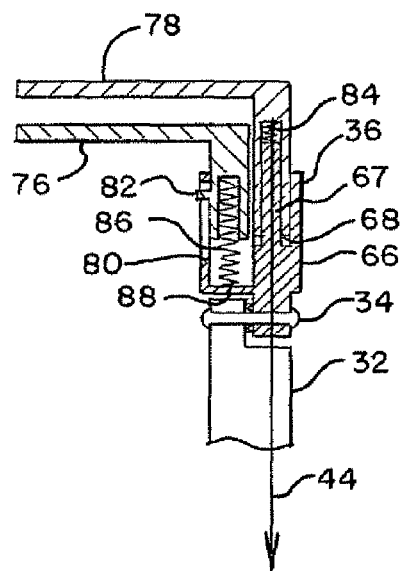

Turning to FIGS. 7A and 7B, there has seen a sixth embodiment of an actuation mechanism for a graspers according to the present invention. To the extent that the embodiment of FIGS. 7A and 7B is similar to those embodiments previously described, like reference numerals are used to designate corresponding structure. The grasper includes a shaft 32 to which a jaw mounting assembly 66 is pivotally secured, such as by a pin or rivet 34. The mounting assembly 66 includes an integral sleeve member 36 that slidably receives both jaw members 76 and 78. The sleeve 36 includes an elongated slot 80 that receives a tab 82 that extends from the jaw member 76. The slot 80 and tab 82 help to ensure that the jaw member 76 slides smoothly with respect to the sleeve 36 and that proper orientation of the jaw member 76 is maintained during such sliding movement.

The mounting assembly also includes a post or rod 67 with a relieved or reduced diameter end portion that defines a shoulder 68 and on which the jaw member 78 is slidably seated. A compression spring 84 is interposed between the post 66 and the jaw 78 to bias the jaw 78 away from the jaw member 76 to the open position shown in FIG. 7A. To move jaw member 78 from its open to its closed position, a length of cable 44 extends from the handle through the shaft 32 and is attached on one end to the actuating lever 56 and the other end to the jaw member 78. Thus, when the lever 56 is actuated to move the jaw member 78 to the closed position, tension is applied to the cable 44 to pull the jaw member 78 down onto the relieve portion of the post against the force of the spring 84. When tension on the cable 44 is released, the spring 84 returns the jaw member 78 back to the position shown in FIG. 7A.

In order to control the force exerted on tissue captured between the closed jaws 76 and 78, a compression spring 86 is interposed between jaw member 76 and a bottom wall 88 on the sleeve 36. The compression spring 86 biases the jaw member 76 toward the jaw member 78. As the jaws 76 and 78 are closed on tissue, the degree to which spring 86 is compressed controls the force exerted on tissue captured between the jaws. Using the terminology used throughout this description, and as described above, jaw 78 may be referred to as the movable jaw member, as that is the jaw member directly moved by the operator via cable 44, and jaw member 76 may be referred to as the fixed jaw member, although it is movable in response to clamping to limit the force exerted on the tissue captured between the jaws as permitted by spring 86.

Figure 8A:
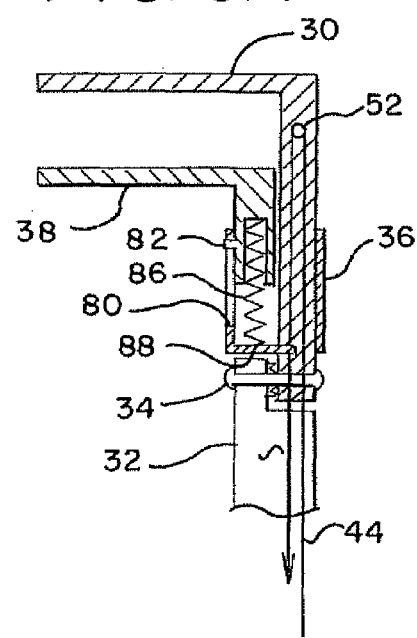
FIGS. 8A and 8B are fragmentary, cross-sectional views of a seventh embodiment of an actuation mechanism according to the present invention showing the jaws in the open and closed positions, respectively.
Figure 8B:
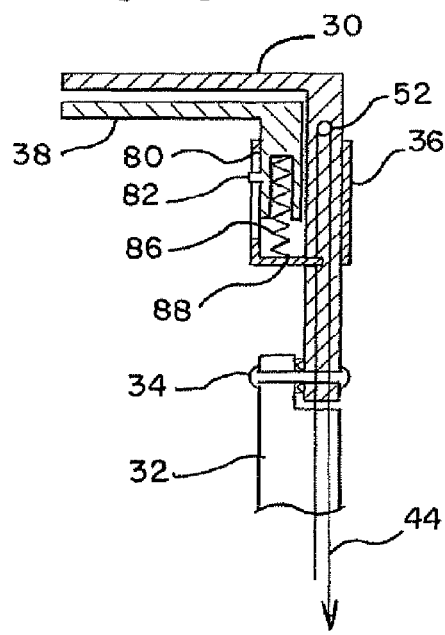

Turning to FIGS. 8A and 8B, there is seen a seventh embodiment of an actuation mechanism for a graspers according to the present invention. To the extent that similar structure to that previously described is utilized in the embodiment of FIGS. 8A and 8B, corresponding reference numerals are used.

In FIGS. 8A and 8B, a fixed jaw member 30 is pivotally attached to the grasper shaft 32, such as by a pin or rivet 34. A movable jaw member 38 is slidably secured to the fixed jaw member 30 by means of sleeve member 36. To effect movement of the movable jaw member 38 between the open and closed positions, a length of cable 44 in the form of an endless loop extends between the handle and the fixed jaw member 30, where it is trained about pulley 52. The cable 44 is secured to a proximal end wall 88 on the sleeve 36 and to the trigger or lever 56. Accordingly, as the trigger 56 rotates about its pivot, the cable 44 moves the sleeve 36, and consequently the movable jaw member 38, between the open and closed position shown in FIGS. 8A and 8B.

In order to control the force exerted on tissue captured between the closed jaw members 30 and 38, a compression spring 86 interposed between the movable jaw member 38 and the bottom wall 88 on the sleeve 36. The compression spring 86 biases the movable jaw member 38 toward the fixed jaw member 30. As the jaw members 30, 38 are closed on tissue, the movable jaw member slides downwardly or into the sleeve 36 against the force of the spring 86. To ensure a smooth and accurate sliding motion, the sleeve 36 includes an elongated slot 80 that receives a tab 82 that extends from the movable jaw member 38. The degree to which the spring 86 is compressed controls the force exerted on tissue captured between the jaw members 30 and 38.

Figure 9A:
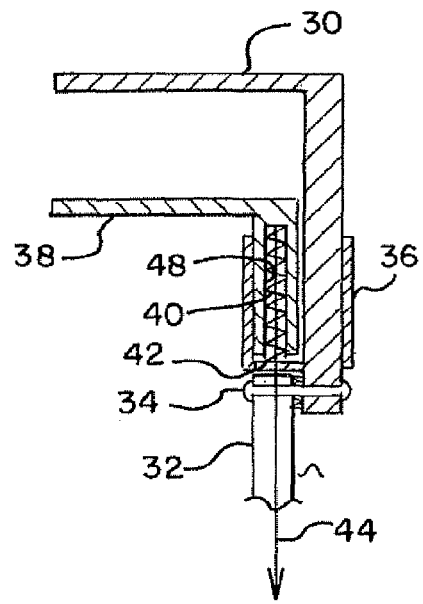
FIGS. 9A and 9B are fragmentary, cross-sectional views of an eighth embodiment of an actuation mechanism according to the present invention showing the jaws in the open and closed positions, respectively.
Figure 9B:
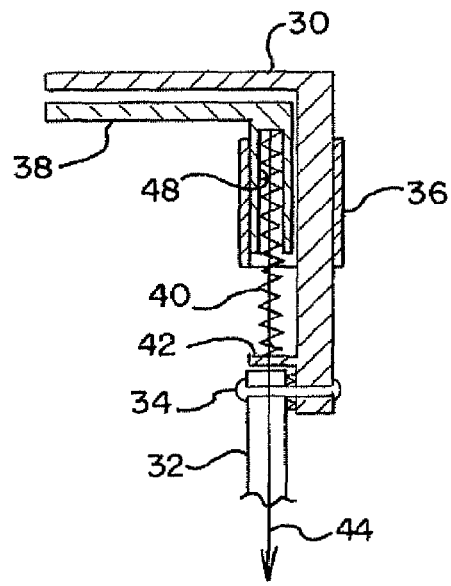

Turning to FIGS. 9A and 9B, where is seen an eighth embodiment of an actuation mechanism for a graspers according to the present invention. Again, to the extent that the structure of this embodiment is similar to the previously-described embodiments, identical reference numerals are used.

The grasper of FIGS. 9A and 9B includes an outer, fixed jaw member 30 pivotally secured to the grasper shaft 32, such by a pin or rivet 34 or similar hinge. A separate slidable sleeve member 36 is carried by the fixed jaw member 30, with the movable jaw member 38 being mounted to the interior of sleeve 36 so that the movable jaw member 38 and the sleeve 36 move in unison with respect to the fixed jaw 30. A compression spring 40 is seated in a recess or bore 48 in the movable jaw member 38 and captured between the movable jaw member 38 and an arm or stop member 42 extending from the fixed jaw member 30. The spring 40 biases the assembly of the movable jaw member 38/sleeve member 36 toward the fixed jaw member 30. The movable jaw member 38/sleeve member 36 assembly is maintained in the open position by an actuating device, such as cable 44, that extends from the lever 56 to the movable jaw member 38. When the lever is actuated, tension is released on the cable 44 that maintains the jaw members 30 and 38 in their open position against the force of the compressed spring. The spring 40 then moves the movable jaw member 38 to the closed position. The force exerted on tissue held between the closed jaw members 30 and 38 depends on the thickness of the tissue and the spring constant for the spring 40.

Figure 10A:
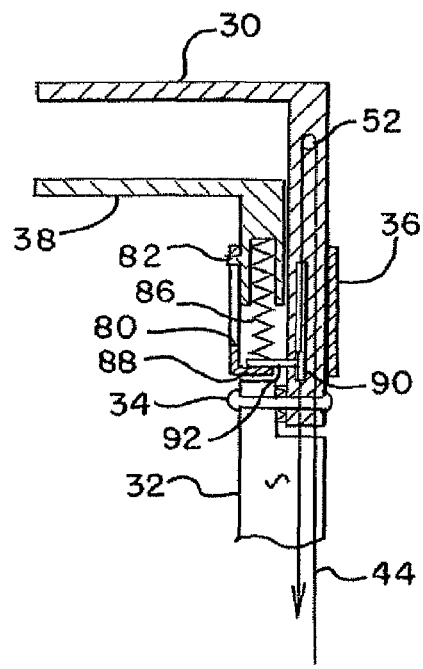
FIGS. 10A and 10B are fragmentary, cross-sectional views of a ninth embodiment of an actuation mechanism according to the present invention showing the jaws in the open and closed positions, respectively.
Figure 10B:
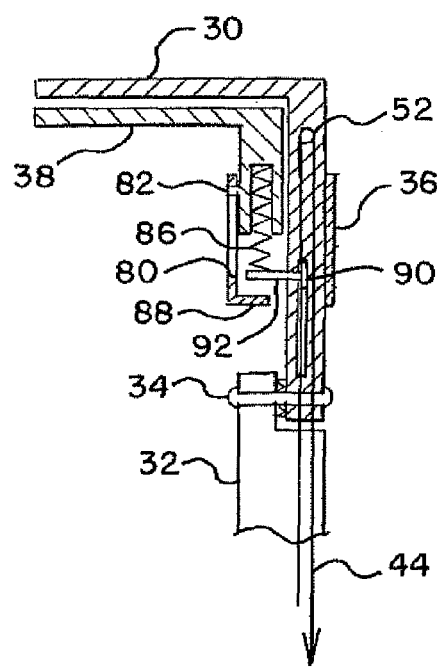

Turning to FIGS. 10A and 10B, there is seen a ninth embodiment for an actuation mechanism for a graspers according to the present invention. Again, to the extent that the embodiment of FIGS. 10A and 10B employ structure previously described, the same reference numerals are used.

A fixed jaw 30 is pivotally secured to the grasper shaft 32 by such as a pin or rivet 34. A movable jaw member 38 is slidably secured to the fixed jaw member 30 by means of slidable sleeve 36. An actuating device such as a length of cable 44 in the form of an endless loop extends between the handle, where it is secured to the lever 56, and the fixed jaw member 38, where it is trained about pulley 52. The cable 44 has a traveler or actuator 90 secured thereto within the fixed jaw. The traveler 90 includes an integral arm 92 that extends outwardly from the fixed jaw member 30 into the interior of the sleeve member 36.

A compression spring 86 is interposed between the arm 92 of the traveler 90 and the movable jaw member 38. The spring 86 biases the movable jaw member 38 toward the fixed jaw member 30. Accordingly, as the cable 44 moves about the pulley 52 in response to actuation of the lever 56, the traveler 90 moves in unison therewith to move the movable jaw member 38/sleeve 36 assembly between the open and closed positions with respect to the fixed jaw member 30.

The sleeve 36 also includes an end wall or stop member 88 that is adapted to engage the arm 92 on the traveler 90, thus limiting relative movement between the sleeve 36 and the traveler 90, and to allow opening of the jaws. When in the closed position, the compression spring 86 regulates the force exerted on tissue between the closed jaw members 30 and 38. Relative movement between the movable jaw member 38 and the sleeve 36 is also accommodated. To this end, the sleeve 36 includes an elongated slot 80 that receives a tab 82 on the movable jaw member 38. The slot 80/tab 82 limit the range of relative movement between the movable jaw member 38 and sleeve 36, as well as ensuring smooth and accurate sliding motion.

While the invention has been described in terms of certain preferred embodiments, there is no intention to limit the invention to the same. Instead, the invention is defined by the scope of the following claims.

What is claimed:

1. A device for clamping tissue comprising:
a handle;
an elongated shaft having proximal and distal ends and being secured to the handle at the proximal end;
first and second jaw members carried at the distal end of the shaft and having opposed clamping surfaces;
the second jaw member being slidably moveable relative to the first jaw member so the jaw members can be moved between an open position in which the clamping surfaces are spaced apart and a closed position in which the clamping surfaces are spaced apart an amount less than that in the open position, wherein the second jaw member being secured to the first jaw member by a sleeve, the second jaw member being slidably received within the sleeve;
an actuating member extending from the handle to one of the jaw members for moving the jaw members between the open and closed positions;
a first resilient member associated with at least a selected one of the first jaw member, second jaw member, and the actuating member, the first resilient member being positioned to limit the force exerted on tissue held between the clamping surfaces of the jaws when the jaws are in the closed position; and
a second resilient member operable to bias the second jaw member to the open position.

2. The device of claim 1 wherein the first jaw member is pivotally secured to the elongated shaft.

3. The device of claim 2 wherein the first jaw is pivotable with respect to the elongated shaft by remote actuation.

4. The device of claim 1 wherein the resilient member is a spring.

5. The device of claim 1 wherein the shaft is malleable so that it may be formed by a user into a desired shape.

6. The device of claim 1 wherein the clamping surface of each of the first and second jaw members includes an elongated electrode.

7. The device of claim 1 in which the first resilient member comprises an extension spring and the second resilient member comprises a compression spring disposed between the first and second jaw members.

8. The device of claim 1 in which the first jaw is a fixed jaw mounted to the shaft, the device further comprising a sleeve associated with the fixed jaw, and the second jaw being slidably secured to the fixed jaw by the sleeve, the actuating member comprising a cable extending from the handle through the elongated shaft and secured to the moveable jaw; the device further comprising a trigger pivotally secured to the handle and connected to the cable, and the resilient member comprising a first spring interposed between the cable and the moveable jaw; whereby manipulation of the trigger actuates the cable to move the moveable jaw between an open and closed position with respect to the fixed jaw, the first spring regulating the amount of force exerted on tissue held between the jaws when the moveable jaw is in the closed position.

9. The device of claim 8 wherein the fixed jaw is pivotally mounted to the shaft.

10. The device of claim 8 further comprising a second spring interposed between the fixed jaw and the moveable jaw to bias the moveable jaw towards its open position.

11. The device of claim 8 wherein a first length of the cable connects the trigger to the first spring and the first spring is connected directly to the moveable jaw.

12. The device of claim 8 wherein a first length of the cable connects the trigger to the first spring and a second length of the cable connects the spring to the moveable jaw, the first spring being located within the elongated shaft or handle.

13. A device for clamping tissue comprising:
a handle;
an elongated shaft secured to the handle;
a first jaw pivotally mounted to the elongated shaft;
a moveable jaw slidably mounted to the first jaw;
a first trigger movably secured to the handle;
a first actuating member that operably communicates between the handle and the moveable jaw so that moving the trigger moves the moveable jaw between open and closed positions relative to the first jaw;
a first resilient member interposed along the actuating member, the first resilient member being positioned to limit the amount of force exerted on tissue held between the jaws when the moveable jaw is in the closed position; and
a second resilient member interposed between the handle and the first trigger to bias the trigger in a direction to move the moveable jaw toward the open position.

14. The device of claim 13 in which the actuating member comprises a length of cable forming a loop extending between the handle and the first jaw and trained about a first pulley associated with the handle and a second pulley associated with the first jaw, the cable being secured to both the trigger and the moveable jaw so that moving the trigger moves the moveable jaw between open and closed positions with respect to the first jaw.

15. The device of claim 13 and further comprising a second trigger movably secured to the handle and secured to a second actuating member that communicates from the second trigger to the first jaw, whereby moving the second trigger causes the second actuating member to pivot the first jaw with respect to the elongated shaft.

16. The device of claim 13 in which the first and second resilient members comprise coil springs.

17. A device for clamping tissue comprising: a handle; an elongated shaft secured to the handle; a jaw-mounting member, which member is carried at the distal end of the shaft; a first jaw moveably secured to the mounting member; a second jaw moveably secured to the mounting member; a first trigger movably secured to the handle; a first actuating member that operably communicates between the handle and one of the jaws so that moving the trigger moves such jaw between open and closed positions with respect to the other jaw; and a resilient member disposed between the other jaw and the mounting member for regulating the amount of force exerted on tissue held between the jaws when the one jaw is moved to the closed position.

18. The device of claim 17 wherein the mounting member is pivotally mounted to the elongated shaft and further comprising a second trigger movably secured to the handle and a second actuating member operably connecting the second trigger to the mounting member, whereby moving the second trigger causes the mounting member to pivot with respect to the elongated shaft.

19. The device of claim 17 in which the first actuating member comprises a length of cable forming a loop extending between the handle and the mounting member and trained about a first pulley associated with the handle and a second pulley associated with the mounting member, the cable being secured to both the trigger and the second jaw so that moving the trigger moves the second jaw between open and closed positions with respect to the first jaw.

20. A device for clamping tissue comprising: a handle; an elongated shaft secured to the handle; a trigger movably mounted to the handle; a jaw-mounting member mounted to the shaft; a first jaw slidably mounted with respect to the jaw-mounting member; a second jaw slidably mounted with respect to the jaw-mounting member; an actuating member connecting the trigger to the second jaw for moving the second jaw from an open position to a closed position with respect to the first jaw; a first resilient member interposed between the second jaw and the jaw-mounting member biasing the second jaw toward the open position; and a second resilient member interposed between the first jaw and the jaw mounting member biasing the first jaw toward the second jaw and for regulating the amount of force exerted on tissue held between the jaws when the second jaw is moved to the closed position.

21. A device for clamping tissue comprising: a handle; an elongated shaft secured to the handle; a trigger movably secured to the handle; a fixed jaw secured to the shaft; a sleeve slidably secured to the fixed jaw; a moveable jaw slidably received in the sleeve; an actuating member operatively connecting the trigger and the sleeve so that moving the trigger moves the sleeve and the moveable jaw carried thereby between open and closed positions with respect to the fixed jaw; and a resilient member interposed between the sleeve and the moveable jaw biasing the moveable jaw toward the fixed jaw and regulating the amount of force exerted on tissue held between the jaws when the moveable jaw is moved to the closed position.

22. The device of claim 17 wherein the jaw-mounting member is pivotally mounted to the shaft.

23. The device of claim 18 wherein the fixed jaw is pivotally secured to the shaft.

24. A device for clamping tissue comprising: a handle; an elongated shaft secured to the handle; a trigger movably secured to the handle; a fixed jaw secured to the elongated shaft; a sleeve slidably associated with the fixed jaw; a moveable jaw carried by the sleeve; an actuating member operatively connecting the trigger and the moveable jaw for moving the moveable jaw from a closed position to an open position; a resilient member interposed between the fixed jaw and the moveable jaw biasing the moveable jaw toward the closed position and for regulating the amount of force exerted on tissue held between the jaws and the second jaw is in the closed position.

25. The device of claim 24 wherein the fixed jaw is pivotally secured to the elongated shaft.

26. A device for clamping tissue comprising: a handle; an elongated shaft; a trigger movably secured to the handle; a fixed jaw secured to the shaft; a sleeve slidably associated with the fixed jaw; a moveable jaw slidably received by the sleeve; a length of cable secured to the trigger and forming a loop extending between the handle and the fixed jaw, the cable being trained about a first pulley associated with the handle and a second pulley associated with the fixed jaw; an actuator associated with the fixed jaw and secured to the cable, the actuator being moveable between first and second positions with respect to the fixed jaw by pivoting the trigger member; and a resilient member interposed between the actuator and the moveable jaw so that the actuator is moved between the first and second positions, the moveable jaw is moved between open and closed positions, the resilient member regulating the force exerted on tissue held between the jaws when the moveable jaw is moved to the closed position.

27. The device of claim 26 wherein the sleeve defines an interior region and the actuator extends into the interior region of the sleeve, the relative movement of the actuator with respect to the sleeve being limited by a first stop member associated with the sleeve.

28. The device of claim 27 wherein the relative movement between the sleeve and the moveable jaw is limited by a second stop member.

29. The device of claim 26 wherein the fixed jaw is pivotally secured to the shaft.

* * * * *